United States Patent
Hara et al.

(10) Patent No.: US 10,149,802 B2
(45) Date of Patent: Dec. 11, 2018

(54) FILLER CHARACTERIZED BY ACIDIC POLYMER TREATMENT METHOD

(71) Applicant: SHOFU INC., Kyoto (JP)

(72) Inventors: Daisuke Hara, Kyoto (JP); Toshiyuki Nakatsuka, Kyoto (JP); Yusei Kadobayashi, Kyoto (JP)

(73) Assignee: SHOFU INC., Kyoto (JP)

( * ) Notice: Subject to any disclaimer, the term of this patent is extended or adjusted under 35 U.S.C. 154(b) by 0 days.

(21) Appl. No.: 15/001,579

(22) Filed: Jan. 20, 2016

(65) Prior Publication Data

US 2016/0213576 A1 Jul. 28, 2016

(30) Foreign Application Priority Data

Jan. 22, 2015 (JP) ................... 2015-010736

(51) Int. Cl.
| | |
|---|---|
| *A61K 6/00* | (2006.01) |
| *C03C 4/00* | (2006.01) |
| *C09C 3/12* | (2006.01) |
| *C03C 3/118* | (2006.01) |
| *C03C 12/00* | (2006.01) |
| *C03C 17/34* | (2006.01) |
| *C09C 1/28* | (2006.01) |

(52) U.S. Cl.
CPC ............ *A61K 6/0091* (2013.01); *C03C 3/118* (2013.01); *C03C 4/0021* (2013.01); *C03C 12/00* (2013.01); *C03C 17/3405* (2013.01); *C09C 1/28* (2013.01); *C09C 3/12* (2013.01)

(58) Field of Classification Search
CPC .................................................. A61K 6/0091
See application file for complete search history.

(56) References Cited

U.S. PATENT DOCUMENTS 6,620,861 B1    9/2003  Nakatuka et al.

FOREIGN PATENT DOCUMENTS

| EP | 2 949 310 | 12/2015 | |
|---|---|---|---|
| JP | 2001-139844 | 5/2001 | |
| JP | 2001-322908 | 11/2001 | |
| JP | 2002-114620 | 4/2002 | |
| JP | 2002-145715 | 5/2002 | |
| JP | 5653549 B1 * | 1/2015 | ........... A61K 6/0017 |

OTHER PUBLICATIONS

English machine translation of Sadakane et al. (JP 5653549); translated May 15, 2017.*
Office Action dated Mar. 9, 2015 in corresponding Japanese Application No. JP 2015-010736, with English Translation.
Extended European Search Report dated May 19, 2016 in corresponding European Application No. 16151826.1.

* cited by examiner

*Primary Examiner* — Michael F Pepitone
(74) *Attorney, Agent, or Firm* — Wenderoth, Lind & Ponack, L.L.P.

(57) ABSTRACT

The present invention relates to a deagglomerated glass filler for sustained ion release for imparting ion sustained-release property to a dental material for use in the dental field. The dental material means a material for use in filling, prosthetic repair, temporary sealing, temporary bonding, preparation of a prosthetic appliance, adhesion/luting, pit and fissure sealing, or the like in a dental treatment. A glass filler for sustained ion release that sufficiently continuously releases a metal ion present in a glass composition as compared with a conventional glass filler for sustained ion release has been demanded in the field of a dental material. Such an object is achieved by a glass filler for sustained ion release that is obtained by performing a silane compound treatment step and an acidic polymer treatment step and that is controlled to satisfy a specific D50 particle size relationship in each of the steps.

9 Claims, No Drawings

FILLER CHARACTERIZED BY ACIDIC POLYMER TREATMENT METHOD

BACKGROUND OF THE INVENTION

Field of the Invention

The present invention relates to a deagglomerated glass filler for sustained ion release for imparting ion sustained-release property to a dental material for use in the dental field. The dental material means a material for use in filling, prosthetic repair, temporary sealing, temporary bonding, preparation of a prosthetic appliance, adhesion/luting, pit and fissure sealing, or the like in a dental treatment, specific examples thereof include composite resins (including a resin for a facing crown and a resin for restoration), temporary sealing/temporary bonding materials, a resin cement, an adhesive and a fissure sealant, and the dental material can be produced by, for example, mixing of a glass filler for sustained ion release and a polymerizable monomer.

Description of the Related Art

With respect to a conventional glass filler for sustained ion release, a large number of approaches have been made in order to allow metal ions such as fluorine, strontium and boron present in a glass composition. The conventional glass filler for sustained ion release, however, cannot sustainably release ions in sufficient amounts, and also cannot sustainably release ions in a continuous manner.

In Japanese Patent Laid-Open No. 2001-139844, a fluorine sustained-release filler is described which is subjected to a silane compound treatment and an acidic polymer treatment, but the filler particle sizes (MV values) before and after each of such treatments are the same, and as a result, the amount and duration of sustained ion release are not sufficient.

SUMMARY OF THE INVENTION

While the conventional glass filler for sustained ion release sustainably releases various ions, the amounts of such ions sustainably released are small. Therefore, a glass filler for sustained ion release which sustainably releases ions in much larger amounts and also has persistence so that such sustained-release is continued over a long period, has been demanded.

The present inventors have made intensive studies in order to solve the above problem, and as a result, have found that a filler subjected to a silane compound treatment and an acidic polymer treatment is in an agglomerated or granulated state, to thereby affect ion sustained-release property of the filler and persistence of such ion sustained-release. More specifically, the present inventors have found the relationship among the filler particle sizes (MV values) before and after each of the treatments, and ion sustained-release property and persistence of such ion sustained-release, leading to completion of the present invention.

The present invention provides a deagglomerated glass filler for sustained ion release obtained by sequentially performing a silane compound treatment step of coating a surface of a glass filler for sustained ion release with a silane compound to produce a silane compound-treated glass filler for sustained ion release, an acidic polymer treatment step of treating a surface of the silane compound-treated glass filler for sustained ion release with an acidic polymer, to produce an acidic polymer-treated glass filler for sustained ion release, and a deagglomerating step of deagglomerating the acidic polymer-treated glass filler for sustained ion release, wherein the silane compound-treated glass filler for sustained ion release is agglomerated, and a relationship among an MV value (A) of the glass filler for sustained ion release, an MV value (B) of a granulated product of the silane compound-treated glass filler for sustained ion release, and an MV value (C) of the deagglomerated glass filler for sustained ion release satisfies the following formulas:

$(B)/(A) \geq 2$, preferably $(B)/(A) \geq 5$, further preferably $(B)/(A) \geq 10$; and preferably $(C)/(A) \geq 1$.

A glass composition range of the glass filler for sustained ion release is preferably as follows: $SiO_2$: 15 to 35% by mass, $Al_2O_3$: 15 to 30% by mass, $B_2O_3$: 5 to 20% by mass, SrO: 20 to 45% by mass, F: 5 to 15% by mass, and $Na_2O$: 0 to 10% by mass.

A dental material includes the deagglomerated glass filler for sustained ion release to thereby exert a great effect.

The volume average size can be measured by, for example, particle size distribution measurement using a laser diffraction scattering method suitable for measurement of a fine particle, or an analysis by an image processing software of an electron microscopy image. In the present invention, the volume average size is measured by using "Microtrac HRAX100" manufactured by Nikkiso Co., Ltd. and the MV value is adopted.

The effect of preventing a breath odor is exerted and furthermore transparency of enamel is also enhanced by ions sustainably released from the deagglomerated glass filler for sustained ion release of the present invention.

DETAILED DESCRIPTION OF THE PREFERRED EMBODIMENTS

The glass filler for sustained ion release for use in the deagglomerated glass filler for sustained ion release of the present invention sustainably releases a fluoride ion, further preferably sustainably releases at least one ion among a strontium ion, an aluminum ion and a borate ion, more preferably sustainably releases a fluoride ion, a strontium ion and a borate ion.

The ion sustained-release from the above glass filler for sustained ion release means persistent sustained-release of ions based on elements included in a glass composition constituting the glass filler for sustained ion release, and is different from temporary release of ions in large amounts due to dissolution of metal fluoride and the like in water.

As the glass composition constituting the glass filler for sustained ion release for use in the deagglomerated glass filler for sustained ion release of the present invention, any glass composition can be used without any limitation as long as such a glass composition includes one or more glass backbone formation elements for forming a glass backbone and one or more glass modification elements for modifying a glass backbone. In the above glass composition, a so-called glass amphoteric element serving as both the glass backbone formation element and the glass modification element depending on the glass composition is included in the category of the glass backbone formation element. Specific examples of the glass backbone formation element included in the glass composition constituting the glass filler for sustained ion release include silica, aluminum, boron and phosphorus, and such elements can be used not only singly but also in combinations of a plurality thereof. Specific examples of the glass modification element include halogen elements such as fluorine, bromine and iodine, alkali metal elements such as sodium and lithium, and alkali earth metal elements such as calcium and strontium, and such elements can be used not only singly but also in combinations of a plurality thereof. Among them, a glass composition including silica, aluminum and boron as the glass backbone formation elements and including fluorine, sodium and strontium as the glass modification elements is preferably used in the glass filler for sustained ion release, and specific examples of such a glass composition include a silica glass, a fluoroaluminosilicate glass, a fluoroborosilicate glass and a fluoroaluminoborosilicate glass including strontium and sodium. Furthermore, it is more preferable in the present invention to sustainably release a fluoride ion, a strontium ion, an aluminum ion and a borate ion, therefore specific examples of the glass composition include a fluoroaluminoborosilicate glass including sodium and strontium, and the glass composition range is as follows: $SiO_2$: 15 to 35% by mass, $Al_2O_3$: 15 to 30% by mass, $B_2O_3$: 5 to 20% by mass, SrO: 20 to 45% by mass, F: 5 to 15% by mass, and $Na_2O$: 0 to 10% by mass. The glass composition can be confirmed by using an instrumental analysis such as an elemental analysis, and raman spectrum and fluorescent X-ray analyses, and any of such analyses can be adopted without any problem as long as the measured value is matched to the glass composition range.

A method for producing a glass as a starting material of the glass filler for sustained ion release for use in the deagglomerated glass filler for sustained ion release of the present invention is not particularly limited, and the glass can be produced by a production method such as a melting method or a sol-gel method. Among them, a production method by a melting method using a melting furnace is preferable from the viewpoint of ease of design of the glass composition, including raw material selection.

The structure of the glass produced above is preferably an amorphous structure, and may partially include a crystalline structure without any problem. Furthermore, a mixture of a glass having an amorphous structure and a glass having a crystal structure may be used without any problem. Whether the structure of the glass is an amorphous structure can be determined using an X-ray diffraction analysis or an analysis instrument such as a transmission electron microscope. In particular, the deagglomerated glass filler for sustained ion release of the present invention sustainably releases various ions by means of an equilibrium relation with ion concentrations in the external environment, and therefore the structure of the glass as the starting material constituting the glass filler for sustained ion release is preferably an amorphous structure which is a homogeneous structure.

The glass filler for sustained ion release for use in the deagglomerated glass filler for sustained ion release of the present invention can be obtained by pulverizing the glass as the starting material. The amounts of various ions to be sustainably released from the deagglomerated glass filler for sustained ion release of the present invention are affected by the MV value as a particle size index of the filler, and it is thus important to control the MV value of the glass filler for sustained ion release for use in the deagglomerated glass filler for sustained ion release. The MV value of the glass filler for sustained ion release must be controlled by subjecting the glass as the starting material of the glass filler for sustained ion release to wet and/or dry pulverization, deagglomeration, classification, sieving, and the like. The MV value (A) of the glass filler for sustained ion release for use in the present invention is not particularly limited as long as it is in the range from 0.01 to 100 µm, and the MV value (A) is preferably in the range from 0.01 to 50 µm, further preferably in the range from 0.1 to 5 µm. The filler may be in any shape such as spherical, plate-like, fragmentary or scale-like and is not particularly limited in shape, but is preferably spherical or fragmentary.

In order to increase ion sustained-release property of the deagglomerated glass filler for sustained ion release of the present invention, it is important to functionalize the surface of the glass filler for sustained ion release by a surface treatment, thereby enhancing the ion sustained-release property. Specific examples of a surface treatment material for use in the surface treatment include a surfactant, an aliphatic acid, an organic acid, an inorganic acid, a monomer, a polymer, various coupling materials, a silane compound, a metal alkoxide compound, and a partially condensed product thereof. In particular, it is more preferable to perform a surface treatment with a silane compound and thereafter perform a surface treatment with an acidic polymer.

Next, the silane compound treatment step of coating a surface of the glass filler for sustained ion release with a silane compound to produce a silane compound-treated glass filler for sustained ion release is described.

Into an aqueous dispersion containing a glass filler for sustained ion release pulverized and/or deagglomerated so as to have a desired MV value is mixed a silane compound represented by the following general formula (I):

[Formula 1]

(I)

(wherein Z represents $RO^-$, X represents halogen, Y represents $OH^-$, R represents an organic group having 8 or less carbon atoms, n, m and L each represent an integer of 0 to 4, and n+m+L=4 is satisfied), and is subjected to hydrolysis or partial hydrolysis in the system to provide a silanol compound, and the silanol compound is then condensed and the surface of the glass filler for sustained ion release is covered therewith. As a result, a solid or granulated product of the silane compound-treated glass filler for sustained ion release can be obtained.

In the above silane compound treatment step, hydrolysis and condensation of the silane compound and a polysiloxane treatment of the glass surface are simultaneously performed in the same system, but even a surface treatment method in which hydrolysis and condensation of the silane compound are performed in separate systems to generate a low-condensed silane compound (oligomer) and the oligomer is mixed with the aqueous dispersion containing the glass filler for sustained ion release can also effectively form a polysiloxane coating on the surface of the glass filler for sustained ion release. A polysiloxane treatment method is more preferable in which a commercially available low-condensed silane compound (oligomer) is used and mixed through no process of generating a low-condensed product. The reason why this method is preferable is because, in the case of use of a silane compound monomer, water is present in a large amount in the polysiloxane treatment step, and therefore condensation occurs in a three-dimensional manner and, as a result, self-condensation predominantly progresses to make it impossible to form a uniform polysiloxane coating on the glass surface.

On the other hand, when the low-condensed silane compound (oligomer) is used, a polysiloxane coating can be uniformly formed on the glass surface by a unit having a polysiloxane main chain of a certain length. While the shape of the low-condensed silane compound (oligomer) is not particularly limited, a linear shape is better than a three-dimensional shape. A higher degree of polymerization, i.e., a longer shape is poorer in condensation reactivity and reduces formation of a polysiloxane coating on the surface of the glass filler for sustained ion release, and therefore the degree of polymerization is preferably in the range from 2 to 20, more preferably 2 to 6. The molecular weight here is in the range from 500 to 600.

The polysiloxane treatment in the above aqueous dispersion is performed with stirring at a relatively low speed, the temperature is in the range from room temperature to 100° C., more preferably in the range from room temperature to 50° C., and the stirring time is usually in the range from several minutes to several ten hours, more preferably in the range from 30 minutes to 4 hours. No special method is required in such stirring, and facilities commonly used in general industries can be adopted and used. For example, a stirring machine that can stir a slurry, such as a universal mixing and stirring machine or a planetary mixer may be used for such stirring. Any stirring temperature can be adopted without any problem as long as the temperature is a temperature at which the aqueous medium is not volatilized, namely, a temperature equal to or lower than the boiling point of the aqueous medium. The stirring time must be regulated until gel formation, because the speed of gelation by condensation is affected by the type or amount of the silane compound or low-condensed silane compound to be added, the type of the glass, the MV value thereof and the proportion thereof in the aqueous dispersion, and the type of the aqueous medium and the proportion thereof in the aqueous dispersion. The stirring speed is required to be low because too high a stirring speed causes a gel structure to be broken and inhibits formation of a uniform coating.

The above aqueous medium is constituted of water and an alcohol. The alcohol is added to thereby exert a great effect of reducing agglomeration of the glass filler for sustained ion release in a drying step to further promote deagglomeration. A preferable alcohol includes alcohols having 2 to 10 carbon atoms, but an alcohol having 10 or more carbon atoms has a high boiling point and requires a long time to remove the solvent by drying. Specific alcohols include ethyl alcohol, n-propyl alcohol, isopropyl alcohol, n-butyl alcohol, t-butyl alcohol, iso-butyl alcohol, n-pentyl alcohol, iso-amyl alcohol, n-hexyl alcohol, n-heptyl alcohol, n-octyl alcohol and n-dodecyl alcohol, and an alcohol having 2 to 4 carbon atoms, such as ethyl alcohol, n-propyl alcohol or iso-propyl alcohol is suitably used. The amount of the above alcohol to be added is 5 to 100 parts by weight, preferably 5 to 20 parts by weight based on 100 parts by weight of water. If the amount to be added is more than 100 parts by weight, there may occur a problem that the drying step is complicated. If the amount to be added is less than 5 parts by weight, there may occur a problem that the effect of alcohol addition is not sufficiently exerted. The content of the glass is in the range from 25 to 100 parts by weight, preferably in the range from 30 to 75 parts by weight based on 100 parts by weight of the aqueous medium. If the content is more than 100 parts by weight, the gelation speed by condensation is high to hardly form a uniform polysiloxane coating layer, and if the content is less than 25 parts by weight, the glass may be settled and/or phase separation in the aqueous medium may be caused during stirring. The amount of the silane compound to be added depends on the MV value of the glass, and is in the range from 0.1 to 10 parts by weight, preferably in the range from 0.1 to 4 parts by weight based on the glass in terms of $SiO_2$. If the amount to be added is less than 0.1 parts by weight, no effect by formation of a polysiloxane coating layer is exerted to make deagglomeration to primary particles impossible, resulting in agglomerates and if the amount is more than 10 parts by weight, a solid or granulated product after drying is too hard to be deagglomerated.

The system in the state of "gel" is dried to remove the aqueous medium for solidification. The drying includes two stages: aging and baking, the former aims to grow a gel structure and remove the aqueous medium, and the latter aims to reinforce the gel structure. The former is conducted for removing the aqueous medium without imparting strain to the gel structure and therefore is required to be conducted at a standstill, and equipment such as a box type hot air dryer is preferably used. The aging temperature is in the range from room temperature to 100° C., more preferably in the range from 40 to 80° C. If the temperature is lower than room temperature, removal of the aqueous medium is insufficient, and if the temperature is higher than 100° C., the aqueous medium may be rapidly volatilized to cause defects on the gel structure and/or cause peeling from the glass surface. The aging time depends on the capability of the dryer or the like, and therefore any time may be adopted without any problem as long as the aqueous medium can be sufficiently removed.

On the other hand, the baking step is separated into temperature raising and temperature holding. In the former, it is preferable to gradually heat to a target temperature over a long time, and rapid rise of temperature can cause cracking in the gel structure because a gel dispersion has a low heat conductivity. The latter is baking at a constant temperature. The baking temperature is in the range from 100 to 350° C., more preferably in the range from 100 to 200° C.

The aqueous medium is removed from the gel by drying as described above to provide a solidified or granulated product which is contracted. The solidified or granulated product is agglomerates of the glass filler for sustained ion release, but not simple agglomerates of the glass filler for sustained ion release, and polysiloxane formed by condensation is present at individual boundary surfaces between fine particles. Accordingly, in the next step, the solidified or granulated product is deagglomerated to a certain particle size (MV value), but it is not required to be deagglomerated to the particle size corresponding to the glass filler for sustained ion release before the polysiloxane treatment and may be in the state of being granulated, without any problem. The silane compound-treated glass filler for sustained ion release may be subjected to the next acidic polymer treatment step without being deagglomerated at all, depending on circumstances. The solidified or granulated product can be deagglomerated by application of a shear force or an impact force, and the deagglomerating method can be performed by using, for example, a Henschel mixer, a cross rotary mixer or a super mixer.

In the present invention, such deagglomerating is preferably made so that the relationship between the MV value (B) of the silane compound-treated glass filler for sustained ion release and the MV value (A) of the glass filler for sustained ion release satisfies the following formula:

$$(B)/(A) \geq 2, \text{ preferably } (B)/(A) \geq 5, \text{ further preferably}$$
$$(B)/(A) \geq 10, \text{ and preferably } 10000 \geq (B)/(A).$$

The silane compound-treated glass filler for sustained ion release, subjected to the polysiloxane treatment, is different from the original glass filler for sustained ion release in that individual particles are covered with polysiloxane and agglomerated for granulation.

Examples of the silane compound represented by the general formula (I) can include tetramethoxysilane, tetraethoxysilane, tetrapropoxysilane, tetraallyloxysilane, tetrabutoxysilane, tetrakis(2-ethylhexyloxy)silane, trimethoxychlorosilane, triethoxychlorosilane, triisopropoxychlorosilane, trimethoxyhydroxysilane, diethoxydichlorosilane, tetraphenoxysilane, tetrachlorosilane and silicon hydroxide (silicon oxide hydrate), more preferably tetramethoxysilane and tetraethoxysilane, and a condensed product thereof. A condensed product of the silane compound represented by the general formula (I) is more preferable.

A low-condensed product of the silane compound represented by the general formula (I) is more preferable, and is, for example, a low-condensed silane compound obtained by partial hydrolysis and condensation of tetramethoxysilane and tetraethoxysilane. Such a compound can be used singly or in combination.

An organosilane compound can also be added in the polysiloxane treatment as a part of the silane compound represented by the general formula (I). Specific examples of the organosiloxane compound can include methyltrimethoxysilane, ethyltrimethoxysilane, methoxytripropylsilane, propyltriethoxysilane, hexyltrimethoxysilane, vinyltrimethoxysilane, vinyltriethoxysilane, vinyltri(β-methoxyethoxy)silane, γ-methacryloxypropyltrimethoxysilane, γ-glycidoxypropylmethoxysilane, γ-mercaptopropyltrimethoxysilane, γ-aminopropyltriethoxysilane, 3-aminopropyltriethoxysilane, methyltrichlorosilane and phenyltrichlorosilane, particularly preferably methyltrimethoxysilane, ethyltriethoxysilane, vinyltriethoxysilane and phenyltrichlorosilane. Such a compound can be used singly or in combination. The compound, however, has an organic group present in a polysiloxane layer and therefore can undergo strain in formation of the polysiloxane layer, and the problem about mechanical strength can be caused. Therefore, addition of the compound is required to be limited to a small amount. As a part of the silane compound represented by the general formula (I) in the polysiloxane treatment, an alkoxide compound, a halide, a hydrous oxide, a nitride or a carbonate of other metal can also be added.

Next, the acidic polymer treatment step of treating the surface of the silane compound-treated glass filler for sustained ion release with an acidic polymer to produce an acidic polymer-treated glass filler for sustained ion release is described.

The silane compound-treated glass filler for sustained ion release, obtained in the above step, can be subjected to an acidic polymer treatment for a reaction with an acidic polymer, to thereby provide a most preferable acidic polymer-treated glass filler for sustained ion release, for use in the present invention. The acidic polymer treatment can be conducted by use of any equipment commonly used in the art as long as the equipment is a dry fluid type stirring machine, and examples include a Henschel mixer, a super mixer and a high-speed mixer. The reaction of the silane compound-treated glass filler for sustained ion release with the acidic polymer can be conducted by bringing an acidic polymer solution into contact with the glass filler for sustained ion release by impregnation, spraying or the like. For example, the silane compound-treated glass filler for sustained ion release may be allowed to dry flow, and the acidic polymer solution may be dispersed from above and sufficiently stirred in the state where the filler is allowed to flow. The method of dispersing the acidic polymer solution here is not particularly limited, and a dropping or spraying system that can allow for uniform dispersing is more preferable. The reaction is preferably conducted around room temperature, and a higher temperature makes a reaction of an acid-reactive element and the acidic polymer faster, resulting in ununiform formation of an acidic polymer reaction phase.

After a heat treatment, a heat-treated product can be easily deagglomerated by application of a shear force or an impact force, and the deagglomerating method can be performed by, for example, the equipment used in the above reaction.

The solvent for use in preparation of the acidic polymer solution for use in the above reaction can be any solvent without any problem as long as such a solvent is one that dissolves the acidic polymer, and examples include water, methanol, ethanol and acetone. Among them, water is particularly preferable, and can allow an acidic group of the acidic polymer to be dissociated and uniformly reacted with the surface portion of the ion sustained-release glass in the silane compound-treated glass filler for sustained ion release.

The weight molecular weight of the polymer dissolved in the acidic polymer solution is in the range from 2000 to 50000, preferably in the range from 5000 to 40000. A glass filler for sustained ion release treated with the acidic polymer having a weight average molecular weight of less than 2000 tends to have low ion sustained-release property. An acidic polymer having a weight average molecular weight of more than 50000 increases its viscosity in solution, making it difficult to perform the acidic polymer treatment. The concentration of the acidic polymer in the acidic polymer solution is preferably in the range from 3 to 25% by weight, more preferably in the range from 8 to 20% by weight. If the concentration of the acidic polymer is less than 3% by weight, the acidic polymer reaction phase is brittle. On the other hand, if the concentration of the acidic polymer is more than 25% by weight, the polysiloxane layer (porous) is hardly diffused, but is brought into contact with the glass filler for sustained ion release to result in a quick acid-base reaction, and there occurs a problem that curing is initiated during the reaction of the acidic polymer to result in agglomeration. The amount of the acidic polymer solution to be added to the silane compound-treated glass filler for sustained ion release is preferably in the range from 6 to 40% by weight, more preferably 10 to 30% by weight. In terms of this amount to be added, the optimum amount of the acidic polymer is 1 to 7% by weight and the optimum amount of water is in the range from 10 to 25% by weight based on the silane compound-treated glass filler for sustained ion release.

The acidic polymer that can be used for forming the acidic polymer reaction phase under the silane compound layer of the silane compound-treated glass filler for sustained ion release by the above method is a copolymer or homopolymer of a polymerizable monomer having, as an acidic group, an acidic group such as a phosphoric acid residue, a pyrophosphoric acid residue, a thiophosphoric acid residue, a carboxylic acid residue or a sulfonic acid group. Examples of such a polymerizable monomer can include acrylic acid, methacrylic acid, 2-chloroacrylic acid, 3-chloroacrylic acid, aconitic acid, mesaconic acid, maleic acid, itaconic acid, fumaric acid, glutaconic acid, citraconic acid, 4-(meth) acryloyloxyethoxycarbonylphthalic acid, 4-(meth) acryloyloxyethoxycarbonylphthalic anhydride, 5-(meth) acryloylaminopentylcarboxylic acid, 11-(meth)acryloyloxy-1,1-undecanedicarboxylic acid, 2-(meth)acryloyloxyethyl dihydrogen phosphate, 10-(meth)acryloyloxydecyl dihydrogen phosphate, 20-(meth) acryloyloxyeicosyl dihydrogen phosphate, 1,3-di(meth)acryloyloxypropyl-2-dihydrogen phosphate, 2-(meth) acryloyloxyethylphenylphosphoric acid, 2-(meth) acryloyloxyethyl 2'-bromoethylphosphoric acid, (meth) acryloyloxyethylphenyl phosphonate, di(2-(meth) acryloyloxyethyl) pyrophosphate, 2-(meth)acryloyloxyethyl dihydrogen dithiophosphate and 10-(meth) acryloyloxydecyl dihydrogen thiophosphate. Among these polymers, a homopolymer or copolymer of an α, β-unsaturated carboxylic acid, an acid-base reaction of which relatively slowly progresses, is preferable. An acrylic acid polymer, an acrylic acid-maleic acid copolymer and an acrylic acid-itaconic acid copolymer are more preferable.

The deagglomerating step of deagglomerating the acidic polymer-treated glass filler for sustained ion release, produced, is described.

The acidic polymer-treated glass filler for sustained ion release after the acidic polymer treatment step is obtained as a solidified or granulated product. The solidified or granulated product of the acidic polymer-treated glass filler for sustained ion release can be deagglomerated so as to have a size comparable with that of the glass filler for sustained ion release before the polysiloxane treatment. The solidified or granulated product can be easily deagglomerated by application of a shear force or an impact force, and the deagglomerating method can be performed by using, for example, a Henschel mixer, a cross rotary mixer or a super mixer.

In the present invention, the MV value (C) of the deagglomerated glass filler for sustained ion release after the acidic polymer-treated glass filler for sustained ion release is deagglomerated and the MV value (B) of the silane compound-treated glass filler for sustained ion release satisfy the following formulas:

(B)/(C)≥2, preferably (B)/(C)≥5, further preferably (B)/(C)≥10, and preferably 10000≥(B)/(C).

Furthermore, in the present invention, the MV value (C) of the deagglomerated glass filler for sustained ion release after the acidic polymer-treated glass filler for sustained ion release is deagglomerated and the MV value (A) of the glass filler for sustained ion release satisfy the following formula:

preferably(C)/(A)≥1, further preferably 2≥(C)/(A)≥1.

The relationship between the MV value (A) of the glass filler for sustained ion release and the MV value (C) of the deagglomerated glass filler for sustained ion release can satisfy the above formula to thereby provide the above many effects of the present invention as the glass filler for sustained ion release.

The deagglomerated glass filler for sustained ion release of the present invention is characterized by the glass composition which constitutes the glass filler for sustained ion release for use in the silane compound treatment and the acidic polymer treatment so that the deagglomerated glass filler persistently sustainably releases ion species, and is different from one that temporarily releases ion species in large amounts by dissolution of metal fluoride and the like in water.

Whether the deagglomerated glass filler for sustained ion release has ion sustained-release property can be determined by the following procedure.

To 100 g of distilled water is added 0.1 g of the deagglomerated glass filler for sustained ion release, and when the concentrations (F1) of ions sustainably released in distilled water in stirring for 1 hour or the concentrations (F1) of elements based on such ion species, and the concentrations (F2) of ions sustainably released in distilled water in stirring for 2 hours or the concentrations (F2) of elements based on such ion species satisfy the following formula (1), the filler can be preferably considered as having ion sustained-release property. Herein, "F1" and "F2" are each the total value of "concentrations of ions sustainably released in distilled water" and "concentrations of elements based on such ion species" in terms of all the ions or elements.

$$F2 > F1 \times 1.1 \qquad \text{Expression (1)}$$

When a plurality of ions sustainably released from the deagglomerated glass filler for sustained ion release are present, the concentrations of all the ions or the concentrations of all the elements preferably satisfy the formula (1). Even when at least one of the concentrations of ions or at least one of the concentrations of elements satisfies the formula (1), the filler can also be considered as having persistent ion sustained-release property in the present invention. Such ion concentrations and element concentrations can be analyzed by using plasma emission spectrometry, an atomic absorption analysis, an ion chromatographic analysis and an ion selective electrode method (ISE), without particular limitation.

The glass filler for sustained ion release for use in deagglomerating in the present invention has not only ion sustained-release property but also acid neutralizing ability due to the glass composition constituting the glass filler for sustained ion release for use in the silane compound treatment and the acidic polymer treatment. The acid neutralizing ability can be confirmed by measuring the change in pH when 0.1 g of the deagglomerated glass filler for sustained ion release are added to 10 g of an aqueous lactic acid solution whose pH is adjusted to 4.0 and stirred for 5 minutes. The glass filler for sustained ion release can be determined to have the acid neutralizing ability, when indicating a pH of 5.5 or more, more preferably 6.0 or more, most preferably 6.5 or more.

The deagglomerated glass filler for sustained ion release of the present invention is preferably included in a dental material. Even if the dental material is mixed with a matrix mainly made of an acrylic resin, the deagglomerated glass filler for sustained ion release of the present invention can exert any effects including ion sustained-release ability.

The content the deagglomerated glass filler for sustained ion release of the present invention in the dental material is not particularly limited as long as the content in the range from 0.1 to 90% by mass, preferably in the range from 10 to 50% by mass, more preferably in the range from 15 to 40% by mass.

EXAMPLES

The effects of the present invention can be seen by the following test methods and evaluations.

[Measurement Method of MV Value]

The MV value was measured using "Microtrac HRAX100" manufactured by Nikkiso Co., Ltd.

[Ion Sustained-Release Property Test 1]

To 100 g of distilled water was added 0.1 g of the deagglomerated glass filler for sustained ion release or other filler, and the concentrations (F1) of ions sustainably released in distilled water in stirring for 1 hour or the concentrations (F1) of elements based on such ions were analyzed using a fluorine ion selective electrode (Orion 9609BNWP, Thermo Fisher Scientific) and a plasma emission spectrophotometer (ICP-AES; ICPS-8000, Shimadzu Corporation). The same test was performed except that only the stirring time was changed to 2 hours, and the concentrations (F2) of ions or the concentrations (F2) of elements based on such ions were analyzed in the same manner. The concentrations of ions sustainably released from each filler or the concentrations of elements based on such ions, F1 and F2, were compared and evaluated based on the following formulas, and whether the ion sustained-release property was exhibited was determined.

F2>F1: ion sustained-release property was exhibited.

F2≤F1: ion sustained-release property was not exhibited.

[Ion Sustained-Release Property Test 2]

To 100 g of distilled water was added 0.1 g of the deagglomerated glass filler for sustained ion release or other filler, and the concentrations (F1) of ions sustainably released in distilled water in stirring for 1 hour or the concentrations (F1) of elements based on such ions were analyzed using a fluorine ion selective electrode (Orion 9609BNWP, Thermo Fisher Scientific) and a plasma emission spectrophotometer (ICP-AES; ICPS-8000, Shimadzu Corporation). In addition, 10 kg of distilled water and 5 g of the deagglomerated glass filler for sustained ion release or other filler were stirred for 1 hour and then subjected to centrifugation, filtration and drying, to thereby provide a deagglomerated glass filler for sustained ion release or other filler from which various ions were sustainably released. Next, 0.1 g of the deagglomerated glass filler for sustained ion release or other filler from which various ions were sustainably released was added to 100 g of distilled water, and the concentrations (F3) of ions sustainably released in distilled water in stirring for 5 hours or the concentrations (F3) of elements based on such ions were analyzed in the same manner. F1 and F3 which based on ions sustainably released from each filler were compared and evaluated based on the following formulas, and whether the ion sustained-release property was exhibited was determined.

F3>F1: ion sustained-release property was exhibited.

F3≤F1: ion sustained-release property was not exhibited.

[Acid Neutralizing Ability]

The change in pH when 0.1 g of the deagglomerated glass filler for sustained ion release or other filler are added to 10 g of an aqueous lactic acid solution whose pH was adjusted to 4.0 and stirred for 5 minutes was measured. The glass filler for sustained ion release was determined to have the acid neutralizing ability, when indicating a pH of 5.5 or more.

[Breath Odor Measurement]

The following test was performed for five persons as subjects in order to evaluate the suppression effect of a breath odor. Fifty g of a PMMA (polymethyl methacrylate) resin, 10 g of MMA (methyl methacrylate) and 40 g of the deagglomerated glass filler for sustained ion release or other filler were mixed and molded so as to have a size of 15 mm×15 mm×1 mm, and thereafter cured at 120° C. to provide a test piece. Evaluation was made by allowing the test piece to be kept in the oral cavity of each of the subjects for 60 minutes, and comparing the breath odor before keeping and the breath odor after keeping. In comparison of such breath odors, the sulfur compound concentration (VSC value) in the oral cavity, based on hydrogen sulfide, methyl mercaptan, dimethyl sulfide and the like in the expired breath, was measured (XP-Breath-Tron: New Cosmos Electric Co., Ltd.), and the VSC (1) value in the expired breath before keeping and the VSC (2) value in the expired breath after keeping for 15 minutes were compared. As the evaluation results, the rate of reduction in breath odor=(1−VSC (2)/VSC (1))×100 was calculated, and the average value for five persons was calculated.

[Measurement of Transparency of Enamel]

Bovine tooth enamel was processed to a disc shape having a diameter of 5 mm and a thickness of 1.0 mm, and subjected to buffing to provide an initial test piece. The initial test piece was immersed in 100 g of an aqueous lactic acid solution, whose pH was adjusted to 4.0, for 170 hours to provide an acid etching test piece. Next, the acid etching test piece was immersed in 100 g of distilled water, to which 1 g of the deagglomerated glass filler for sustained ion release or other filler was added, for 70 hours to provide an immersed test piece.

The light transmittances of these test pieces (initial test piece, acid etching test piece and immersed test piece) were measured in the wavelength range from 780 nm to 380 nm using "Spectrophotometer U-3200" (manufactured by Hitachi, Ltd.), and compared.

Evaluation was made using the difference (Light transmittance (%) of immersed test piece−Light transmittance (%) of acid etching test piece). A difference of less than 1% was rated as not effective (Not effective), a difference of 2 to 5% was rated as effective (Effective), and a difference of 5 to 10% was rated as highly effective (Highly effective).

Hereinafter, the method for preparing the deagglomerated glass filler for sustained ion release is described.

[Production of Glass Filler for Sustained Ion Release (IG)]

Various raw materials (glass composition: Table 1): silicon dioxide, aluminum oxide, boron oxide, sodium fluoride and strontium carbonate; were uniformly mixed using a ball mill to prepare a raw material mixture, and thereafter the raw material mixture was molten in a melting furnace at 1400° C. The melt was taken out from the melting furnace, and cooled in water to produce a glass. Herein, each composition shown in Table 1 represents the composition in glass filler for sustained ion release (IG). After 4 kg of alumina cobble stones having a diameter of 6 mmφ were loaded into an alumina pot (inner volume: 3.6 L) with a quadruple-barrel vibration mill, 500 g of the glass obtained above was loaded thereinto and pulverized for 40 hours, to provide glass filler for sustained ion release (IG).

The MV value of IG was measured using "Microtrac HRAX100" manufactured by Nikkiso Co., Ltd., and the results were described in Table 1.

[Production of Glass Filler for Sustained Ion Release Treated with Silane Compound (SF)]

The silane compound was loaded to 900 g of water and 100 g of ethanol in the compounding proportion described in Table 1, and the resultant was stirred at room temperature for 2 hours to prepare a low-condensed product. The low-condensed product (1000 g) prepared and 500 g of the above glass filler for sustained ion release were loaded into a universal mixing and stirring machine, and stirred and mixed for 90 minutes. Thereafter, the resultant was subjected to a heat treatment at 140° C. for 30 hours, and then deagglomerated using a Henschel mixer to provide silane compound-treated glass filler for sustained ion release (SF).

The MV value of SF was measured using "Microtrac HRAX100" manufactured by Nikkiso Co., Ltd., and the results were described in Table 1. A case where deagglomerating was not conducted was designated as "Not deagglomerated".

[Production of Deagglomerated Glass Filler for Sustained Ion Release (KF)]

Each acidic polymer described in Table 1 was used to prepare an aqueous acidic polymer solution having each concentration described in Table 1. While 500 g of above SF was stirred using a Henschel mixer, the aqueous acidic polymer solution prepared was used and sprayed. Thereafter, the resultant was subjected to a heat treatment (at 100° C. for 3 hours) to produce an acidic polymer-treated glass filler for sustained ion release. The acidic polymer-treated glass filler for sustained ion release was deagglomerated using a Henschel mixer to provide deagglomerated glass filler for sustained ion release (KF).

The MV value of KF was measured using "Microtrac HRAX100" manufactured by Nikkiso Co., Ltd., and the results were described in Table 1.

The abbreviations of respective compounds shown in Table 1 are as follows.

Silane compound: Tetramethoxysilane (TMS)
Tetraethoxysilane (TES)

Acidic polymer: Polyacrylic acid-average molecular weight 20000 (produced by Nacalai Tesque Inc.: PAA2)

Polyacrylic acid-average molecular weight 40000 (produced by Nacalai Tesque Inc.: PAA4)

Polymethacrylic acid-average molecular weight 20000 (produced by Nacalai Tesque Inc.: PMA2)

Polymethacrylic acid-average molecular weight 40000 (produced by Nacalai Tesque Inc.: PMA4)

The following fillers were used for glass fillers for non-sustained ion release.

Glass filler 1 for non-sustained ion release: Fuselex X (silica filler, MV value=2.1 μm: Tatsumori Ltd., FLX)

Glass filler 2 for non-sustained ion release: Admafine SO-05 as silica filler (silica filler, MV value=1.6 μm: Admatechs, SOC5)

The relationship among the MV value (A) of the glass filler for sustained ion release, the MV value (B) of the silane compound-treated glass filler for sustained ion release and the MV value (C) of the deagglomerated glass filler for sustained ion release was determined by the following formulas, and the results were described in Table 1.

[MV value relationship 1] (B)/(A)
[MV value relationship 2] (B)/(C)
[MV value relationship 3] (C)/(A)

Each product filler was subjected to the tests described above in [Measurement of ion sustained-release for long period], [Measurement of amounts of sustained ion release], [Acid neutralizing ability], [Measurement of breath odor] and [Measurement of transparency of enamel], and the test results were described in Table 1.

TABLE 1

| | | Example 1 | Example 2 | Example 3 | Example 4 | Example 5 | Example 6 | Example 7 | Example 8 | Example 9 | Example 10 |
|---|---|---|---|---|---|---|---|---|---|---|---|
| Glass composition (% by mass) | $SiO_2$ | | | | | 23.8 | | | | | |
| | $Al_2O_3$ | | | | | 16.2 | | | | | |
| | $B_2O_3$ | | | | | 10.5 | | | | | |
| | SrO | | | | | 35.6 | | | | | |
| | $Na_2O$ | | | | | 2.3 | | | | | |
| | F | | | | | 11.6 | | | | | |
| (IG) Average particle size (μm) (A) | | 1.2 | 1.2 | 1.2 | 1.2 | 1.2 | 1.2 | 1.2 | 4.0 | 7.0 | 1.2 |
| Silane compound (%) | TMS | 0.5 | 0.5 | 0.5 | 0.5 | 0.5 | 0.5 | | | | 0.5 |
| | TES | | | | | | | 0.5 | 0.5 | 0.5 | |
| (SF) Average particle size (μm) (B) | | Not deagglomerated | 8.0 | 3.0 | Not deagglomerated | 8.0 | 3.0 | 100.0 | 8.0 | 70.0 | 3.0 |
| Acidic polymer (%) | PAA2 | 12.0 | 12.0 | 12.0 | 12.0 | 12.0 | 12.0 | 12.0 | 12.0 | 12.0 | 6.0 |
| | PAA4 | | | | | | | | | | 6.0 |
| | PMA2 | | | | | | | | | | |
| | PMA4 | | | | | | | | | | |
| (KF) Average particle size (μm) (C) | | 1.2 | 1.2 | 1.2 | 1.5 | 1.5 | 1.5 | 1.5 | 5.0 | 15.0 | 1.5 |
| Particle size relationship 1 | | ∞ | 6.7 | 2.5 | ∞ | 6.7 | 2.5 | 83.3 | 2.0 | 10.0 | 2.5 |
| Particle size relationship 2 | | ∞ | 6.7 | 2.5 | ∞ | 5.3 | 2.0 | 66.7 | 1.6 | 4.7 | 2.0 |
| Particle size relationship 3 | | 1.0 | 1.0 | 1.0 | 1.3 | 1.3 | 1.3 | 1.3 | 1.3 | 2.1 | 1.3 |
| Ion sustained-release property test 1 (F2-F1) (ppm) | F | 0.55 | 0.50 | 0.46 | 0.54 | 0.55 | 0.45 | 0.54 | 0.55 | 0.54 | 0.46 |
| | Na | 0.20 | 0.19 | 0.15 | 0.18 | 0.19 | 0.14 | 0.21 | 0.22 | 0.16 | 0.14 |
| | B | 0.85 | 0.90 | 0.62 | 0.86 | 0.88 | 0.63 | 0.91 | 0.89 | 0.92 | 0.65 |
| | Al | 0.05 | 0.05 | 0.04 | 0.05 | 0.05 | 0.04 | 0.05 | 0.05 | 0.05 | 0.04 |
| | Sr | 0.74 | 0.75 | 0.65 | 0.72 | 0.78 | 0.62 | 0.71 | 0.78 | 0.72 | 0.66 |
| Ion sustained-release property test 2 (F3-F1) (ppm) | F | 1.25 | 1.30 | 0.99 | 1.24 | 1.28 | 1.02 | 1.28 | 1.32 | 1.32 | 1.06 |
| | Na | 0.52 | 0.58 | 0.42 | 0.53 | 0.58 | 0.44 | 0.54 | 0.58 | 0.57 | 0.41 |
| | B | 1.95 | 1.96 | 1.64 | 1.98 | 1.99 | 1.59 | 1.97 | 1.96 | 1.98 | 1.62 |
| | Al | 0.08 | 0.09 | 0.06 | 0.08 | 0.08 | 0.06 | 0.08 | 0.08 | 0.08 | 0.06 |
| | Sr | 1.68 | 1.65 | 1.42 | 1.68 | 1.69 | 1.40 | 1.67 | 1.68 | 1.69 | 1.42 |
| Acid neutralization ability (pH) | | 6.5 | 6.3 | 5.9 | 6.5 | 6.3 | 6.0 | 6.5 | 6.1 | 6.2 | 6.1 |
| Breath odor | | 85.0 | 80.0 | 75.0 | 85.3 | 82.6 | 72.9 | 86.2 | 79.8 | 84.2 | 75.4 |

TABLE 1-continued

|  |  | Example 11 | Example 12 | Example 13 | Example 14 | Example 15 | Comparative Example 1 | Comparative Example 2 | Comparative Example 3 | Comparative Example 4 | Comparative Example 5 |
|---|---|---|---|---|---|---|---|---|---|---|---|
| Glass composition (% by mass) | SiO2 | 23.8 |  |  | 19.8 |  | FLX | SOC5 | 23.8 | 23.8 | 23.8 |
|  | Al2O3 | 16.2 |  |  | 19.8 |  |  |  | 16.2 | 16.2 | 16.2 |
|  | B2O3 | 10.5 |  |  | 11.7 |  |  |  | 10.5 | 10.5 | 10.5 |
|  | SrO | 35.6 |  |  | 35.0 |  |  |  | 35.6 | 35.6 | 35.6 |
|  | Na2O | 2.3 |  |  | 2.3 |  |  |  | 2.3 | 2.3 | 2.3 |
|  | F | 11.6 |  |  | 11.4 |  |  |  | 11.6 | 11.6 | 11.6 |
| (IG) Average particle size (μm) (A) |  | 4.0 | 7.0 | 1.2 | 1.2 | 1.2 | 2.1 | 1.6 | 1.2 | 1.2 | 1.2 |
| Silane compound (%) | TMS | 0.5 | 0.5 | 0.5 | 0.5 | 0.5 | 0.5 | 0.5 |  | 0.5 |  |
|  | TES |  |  |  |  |  |  |  |  |  |  |
| (SF) Average particle size (μm) (B) |  | 12.0 | 50.0 | Not deagglomerated | 8.0 | 3.0 | Not deagglomerated | 8.0 | 1.2 | 1.5 | 1.2 |
| Acidic polymer (%) | PAA2 | 6.0 | 6.0 | 12.0 | 12.0 | 12.0 | 12.0 | 12.0 |  |  | 12.0 |
|  | PAA4 |  |  |  |  |  |  |  |  |  |  |
|  | PMA2 | 6.0 |  |  |  |  |  |  |  |  |  |
|  | PMA4 |  | 6.0 |  |  |  |  |  |  |  |  |
| (KF) Average particle size (μm) (C) |  | 5.0 | 15.0 | 1.2 | 1.2 | 1.2 | 1.2 | 1.2 | 1.2 | 1.5 | 1.2 |
| Particle size relationship 1 |  | 3.0 | 7.1 | ∞ | 6.7 | 2.5 | ∞ | 5.0 | 1.0 | 1.3 | 1.0 |
| Particle size relationship 2 |  | 2.4 | 3.3 | ∞ | 6.7 | 2.5 | ∞ | 6.7 | 1.0 | 1.0 | 1.0 |
| Particle size relationship 3 |  | 1.3 | 2.1 | 1.0 | 1.0 | 1.0 | 0.6 | 0.8 | 1.0 | 1.3 | 1.0 |
| Ion sustained-release property test 1 (F2-F1) (ppm) | F | 0.55 | 0.55 | 0.54 | 0.53 | 0.43 | 0.00 | 0.00 | 0.14 | 0.13 | 0.21 |
|  | Na | 0.20 | 0.21 | 0.21 | 0.20 | 0.15 | 0.00 | 0.00 | 0.06 | 0.05 | 0.07 |
|  | B | 0.89 | 0.90 | 0.92 | 0.89 | 0.64 | 0.00 | 0.00 | 0.30 | 0.28 | 0.45 |
|  | Al | 0.05 | 0.05 | 0.05 | 0.05 | 0.04 | 0.00 | 0.00 | 0.02 | 0.01 | 0.04 |
|  | Sr | 0.74 | 0.72 | 0.78 | 0.77 | 0.61 | 0.00 | 0.00 | 0.27 | 0.25 | 0.35 |
| Ion sustained-release property test 2 (F3-F1) (ppm) | F | 1.29 | 1.36 | 1.34 | 1.32 | 1.01 | 0.00 | 0.00 | 0.21 | 0.23 | 0.42 |
|  | Na | 0.54 | 0.58 | 0.56 | 0.57 | 0.42 | 0.00 | 0.00 | 0.04 | 0.03 | 0.05 |
|  | B | 1.99 | 2.01 | 2.04 | 1.97 | 1.63 | 0.00 | 0.00 | 0.45 | 0.48 | 0.71 |
|  | Al | 0.08 | 0.08 | 0.08 | 0.08 | 0.06 | 0.00 | 0.00 | 0.02 | 0.02 | 0.02 |
|  | Sr | 1.66 | 1.69 | 1.68 | 1.69 | 1.45 | 0.00 | 0.00 | 0.41 | 0.38 | 0.61 |
| Acid neutralization ability (pH) |  | 6.4 | 6.5 | 6.5 | 6.4 | 6.0 | 4.1 | 4.2 | 5.4 | 5.4 | 5.6 |
| Breath odor measurement (%) |  | 82.9 | 85.4 | 83.9 | 84.2 | 76.2 | 0.0 | 0.0 | 48.7 | 52.8 | 62.1 |
| Measurement of transparency of enamel |  | Highly effective | Highly effective | Highly effective | Highly effective | Effective | Not effective | Not effective | Not effective | Not effective | Not effective |

When the acidic polymer-treated glass filler for sustained ion release obtained by coating the surface of the glass filler for sustained ion release with the silane compound and thereafter treating the resultant with the acidic polymer was used, the amounts of ions to be sustainably released were large and the amounts of ions to be sustainably released for a long period were also large. The acidic polymer-treated glass filler for sustained ion release was also excellent in acid neutralizing ability, and was effective for a reduction in breath odor. Furthermore, an increase in transparency of enamel was also confirmed.

It was confirmed that when the MV value of SF was more than 5 μm, the transparency of enamel was further increased.

Provided is a deagglomerated glass filler for sustained ion release exhibiting ion sustained-release property which has not been conventionally exhibited.

Furthermore, the deagglomerated glass filler for sustained ion release can improve an oral cavity environment and also enhances transparency of enamel, and therefore the present invention is an invention that can be industrially applied.

What is claimed is:

1. A method for preparing a deagglomerated glass filler for sustained ion release comprising sequentially performing:
   a silane compound treatment step of coating a surface of a glass filler for sustained ion release with a silane compound to produce a silane compound-treated glass filler for sustained ion release,
   an acidic polymer treatment step of treating the silane compound-treated glass filler for sustained ion release with an acidic polymer to produce an acidic polymer-treated glass filler for sustained ion release, and
   a deagglomerating step of deagglomerating the acidic polymer-treated glass filler for sustained ion release, wherein the silane compound-treated glass filler for sustained ion release is agglomerated, and a relationship among an MV value (A) which is a filler particle size of the glass filler for sustained ion release, an MV value (B) which is a filler particle size of the silane compound-treated glass filler for sustained ion release to be treated with the acidic polymer at the acidic polymer treatment step and an MV value (C) which is a filler particle size of the deagglomerated glass filler for sustained ion release satisfies the following formulas:

(B)/(A)≥2, and (B)/(C)≥2.

2. The method for preparing a deagglomerated glass filler for sustained ion release according to claim 1, wherein a relationship between the MV value (A) which is a filler particle size of the glass filler for sustained ion release and the MV value (C) which is a filler particle size of the deagglomerated glass filler for sustained ion release satisfies the following formula:

(C)/(A)≥1.

3. The method for preparing a deagglomerated glass filler for sustained ion release according to claim 1, wherein a glass composition range of the glass filler for sustained ion release is as follow:

$SiO_2$: 15 to 35% by mass,
$Al_2O_3$: 15 to 30% by mass,
$B_2O_3$: 5 to 20% by mass,
SrO: 20 to 45% by mass,
F: 5 to 15% by mass, and
$Na_2O$: 0 to 10% by mass.

4. The method for preparing a deagglomerated glass filler for sustained ion release according to claim 2, wherein a glass composition range of the glass filler for sustained ion release is as follow:

$SiO_2$: 15 to 35% by mass,
$Al_2O_3$: 15 to 30% by mass,
$B_2O_3$: 5 to 20% by mass,
SrO: 20 to 45% by mass,
F: 5 to 15% by mass, and
$Na_2O$: 0 to 10% by mass.

5. The method for preparing a deagglomerated glass filler for sustained ion release according to claim 1, wherein a relationship among an MV value (A) which is a filler particle size of the glass filler for sustained ion release and an MV value (B) which is a filler particle size of the silane compound-treated glass filler for sustained ion release to be treated with the acidic polymer at the acidic polymer treatment step satisfies the following formulas:

(B)/(A)≥5.

6. The method for preparing a deagglomerated glass filler for sustained ion release according to claim 1, wherein a relationship among an MV value (A) which is a filler particle size of the glass filler for sustained ion release and an MV value (B) which is a filler particle size of the silane compound-treated glass filler for sustained ion release to be treated with the acidic polymer at the acidic polymer treatment step satisfies the following formulas:

(B)/(A)≥10.

7. The method for preparing a deagglomerated glass filler for sustained ion release according to claim 1, wherein a relationship among an MV value (B) which is a filler particle size of the silane compound-treated glass filler for sustained ion release to be treated with the acidic polymer at the acidic polymer treatment step and an MV value (C) which is a filler particle size of the deagglomerated glass filler for sustained ion release satisfies the following formulas:

(B)/(C)≥5.

8. The method for preparing a deagglomerated glass filler for sustained ion release according to claim 1, wherein a relationship among an MV value (B) which is a filler particle size of the silane compound-treated glass filler for sustained ion release to be treated with the acidic polymer at the acidic polymer treatment step and an MV value (C) which is a filler particle size of the deagglomerated glass filler for sustained ion release satisfies the following formulas:

(B)/(C)≥10.

9. The method for preparing a deagglomerated glass filler for sustained ion release according to claim 1, wherein a relationship among an MV value (A) which is a filler particle size of the glass filler for sustained ion release and an MV value (C) which is a filler particle size of the deagglomerated glass filler for sustained ion release satisfies the following formulas:

2≥(C)/(A)≥1.

* * * * *